(12) United States Patent
Spitzer (10) Patent No.: US 8,641,650 B2
(45) Date of Patent: Feb. 4, 2014

(54) WRIST SUPPORT

(76) Inventor: James M Spitzer, Laguna Niguel, CA (US)

( * ) Notice: Subject to any disclaimer, the term of this patent is extended or adjusted under 35 U.S.C. 154(b) by 387 days.

(21) Appl. No.: 12/411,194

(22) Filed: Mar. 25, 2009

(65) Prior Publication Data

US 2010/0249684 A1   Sep. 30, 2010

(51) Int. Cl.
*A61F 5/00* (2006.01)
*A61F 13/00* (2006.01)

(52) U.S. Cl.
USPC ......... 602/21; 602/5; 602/30; 602/60; 602/64

(58) Field of Classification Search
USPC ................. 602/21, 20, 12, 5, 60, 61, 64; 128/878–879, 99.1, 880; 2/16, 910; D11/3, 4; 63/1.12, 1.13; 119/816; 482/45
See application file for complete search history.

(56) References Cited

U.S. PATENT DOCUMENTS

| | | |
|---|---|---|
| 1,227,700 A | 5/1917 | Tucker |
| 1,469,315 A | 10/1923 | Hansard |
| 2,924,458 A | 2/1960 | Barry |
| 3,049,717 A | 8/1962 | Meyer |
| 3,228,035 A | 1/1966 | Davis |
| 3,238,939 A | 3/1966 | Stubbs |
| 3,314,700 A | 4/1967 | Burrell |
| 3,512,776 A | 5/1970 | Thomas, Sr. |
| 3,704,994 A | 12/1972 | Krzewinski et al. |
| 3,779,550 A | 12/1973 | Benoun et al. |
| 3,815,908 A | 6/1974 | Hashimoto |
| 3,829,090 A | 8/1974 | Ensinger |
| 3,910,318 A | 10/1975 | Blakely |
| 3,970,305 A | 7/1976 | Hawkins |
| 4,047,250 A | 9/1977 | Norman |
| 4,088,318 A | 5/1978 | Massman |
| 4,176,840 A | 12/1979 | Lanning |
| 4,183,098 A | 1/1980 | Knowles, Jr. |
| 4,190,906 A | 3/1980 | Patton, Jr. |
| D270,556 S | 9/1983 | Kneisley |
| RE32,566 E | 12/1987 | Patton, Jr. |
| D295,897 S | 5/1988 | Thimm-Kelly |
| 4,798,199 A | 1/1989 | Hubbard et al. |
| 4,829,604 A | 5/1989 | Allen et al. |
| 4,881,533 A | 11/1989 | Teurlings |
| 4,925,187 A | 5/1990 | Fleenor et al. |
| 5,160,314 A | 11/1992 | Peters |
| D339,866 S | 9/1993 | Rice |
| D340,990 S | 11/1993 | Kawamura |
| D357,745 S | 4/1995 | Radwell |
| 5,484,392 A | 1/1996 | Sydor et al. |

(Continued)

FOREIGN PATENT DOCUMENTS

| | | |
|---|---|---|
| EP | 0 162 610 B1 | 6/1988 |
| WO | WO 92/19196 A1 | 11/1992 |
| WO | WO 01/08618 A1 | 2/2001 |

*Primary Examiner* — Kim M Lewis
(74) *Attorney, Agent, or Firm* — Knobbe, Martens, Olson & Bear LLP (57) ABSTRACT

A wrist support worn by a user can diminish or eliminate pain, stress, or discomfort on the wrist and hand regions while lifting various objects of size and weight in a repetitive or non-repetitive manner. The specification describes embodiments of wrist support devices, including a wrist support device that can inhibit wrist extension and flexion, and ulnar and radial deviation, with a support that transfers forces around the wrist muscles and ligaments onto the larger and stronger muscles of the upper and lower arm.

13 Claims, 9 Drawing Sheets

(56) References Cited

U.S. PATENT DOCUMENTS

| | | |
|---|---|---|
| 5,513,657 A | 5/1996 | Nelson |
| 5,538,501 A | 7/1996 | Caswell |
| D379,678 S | 6/1997 | Rosado |
| 5,649,900 A | 7/1997 | Kline |
| 5,708,981 A | 1/1998 | Tilton |
| 5,769,808 A | 6/1998 | Matthijs et al. |
| 5,868,692 A * | 2/1999 | Michniewicz ................. 602/21 |
| 5,980,476 A | 11/1999 | Wiederrich |
| 6,007,508 A * | 12/1999 | Reinhardt et al. ............. 602/62 |
| 6,024,715 A * | 2/2000 | Maxwell ........................ 602/64 |
| D427,383 S | 6/2000 | Inman |
| 6,179,800 B1 * | 1/2001 | Torrens ........................... 602/21 |
| 6,328,706 B1 | 12/2001 | Yattavong |
| D456,081 S | 4/2002 | Bell et al. |
| D461,600 S | 8/2002 | Domanski et al. |
| D461,901 S | 8/2002 | Rodgers |
| 6,540,710 B1 | 4/2003 | Cruz |
| 6,561,994 B1 | 5/2003 | Mills et al. |
| D477,409 S | 7/2003 | Mills et al. |
| D486,610 S | 2/2004 | Alivo, Jr. |
| D496,465 S | 9/2004 | Weaver, II |
| 6,790,192 B2 | 9/2004 | Robinson |
| 6,893,410 B1 | 5/2005 | Hely |
| 6,942,632 B2 | 9/2005 | Cho |
| 7,033,330 B2 | 4/2006 | de Lint |
| 7,033,331 B1 | 4/2006 | Hely |
| 7,867,182 B2 * | 1/2011 | Iglesias et al. ................. 602/20 |
| 2004/0143205 A1 | 7/2004 | Ressel |
| 2005/0101898 A1* | 5/2005 | Cohen ............................ 602/21 |
| 2005/0197608 A1 | 9/2005 | Taylor et al. |
| 2006/0009724 A1 | 1/2006 | Busuttil |
| 2006/0015980 A1 | 1/2006 | Nordt, III et al. |

* cited by examiner

WRIST SUPPORT

BACKGROUND OF THE INVENTION

1. Field of the Invention

The present inventions relate generally to body braces and particularly to braces with features that provide wrist support.

2. Description of the Related Art

Lifting objects can place harmful stress on the wrist. For example, during the process of moving an object from waist-level to above one's head, the weight of the object must be carried by the sensitive and relatively weak ligaments and muscles in the wrist, which consequently may be damaged. The risk of such damage may be particularly prevalent among laborers, such as waiters or construction workers, who frequently must lift objects above shoulder level as part of their employment.

Various braces are used in the region of the wrist. Some braces are too large, heavy, and restrictive, extending from forearm to the upper regions of the hand. Other braces are too small and fail to provide adequate support.

SUMMARY OF THE INVENTION

A wrist support worn by a user can diminish or eliminate pain, stress, or discomfort on the wrist and hand regions while lifting various objects of size and weight in a repetitive or non-repetitive manner. To this end, the disclosed inventions generally seek to inhibit wrist extension and flexion, and ulnar and radial deviation, by means of a support that transfers forces around the wrist muscles and ligaments onto the larger and stronger muscles of the upper and lower arm.

Thus, in accordance with some embodiments disclosed herein, the support can comprise a cuff, such as a rigid cuff made of a hard plastic or other hard material, which generally surrounds and extends across the user's wrist. The cuff can extend a distance on both sides of the user's wrist, toward the fingers and toward the forearm, so that when the cuff is worn, movement of the wrist is diminished or substantially restricted. Because bending of the wrist is limited, when a user wearing the support lifts or moves objects, forces are transferred through the support to the forearm or other muscles of the user. Nevertheless, mobility of the fingers and thumb of the user can be unobstructed because the support is generally contoured about the base of the thumb and palm.

The support can be made in a variety of sizes to fit many individuals. In some embodiments, various cushioning and/or securing means such as O-rings, trapped-air cushions, or elastic can be provided on the interior of the support to provide a more secure and/or comfortably fit to the wearer. Some embodiments include cushioning or padding to offer a more comfortable fit to the user. Some embodiments of the support may be attached and detached from the user with a fastening mechanism, to removably lock the support around a wearer's wrist. Although the support has particular utility for those who often lift objects above the shoulders, the design can also be useful for other applications, including athletics.

BRIEF DESCRIPTION OF THE DRAWINGS

The above-mentioned and other features, aspects, and advantages of the inventions disclosed herein are described below with reference to the drawings. Illustrated embodiment is intended to provide an example but not to limit the inventions. The drawings contain the following figures.

DETAILED DESCRIPTION OF PREFERRED EMBODIMENTS

FIGS. 1-7 illustrate an embodiment of a wrist support 10. The illustrated wrist support 10 can include a hinged-type brace with a clasp. Other embodiments can comprise other types of opening, closing, or securing mechanisms, or can be positioned on the body in some other way. Moreover, although the illustrated embodiment is a support for the left hand, other embodiments include supports for the right hand (in which the design is substantially reversed).

In some embodiments, the support 10 is rigid and can be made of material configured to substantially surround a wearer's wrist. In some embodiments, the support can substantially flex in portions or in a region substantially surrounding the wearer's wrist. The support 10 may be made from many types of materials, such as one or more of ceramics, plastics, rubber and rubber alloys, resins, fabrics, carbon fibers, paper, metal and wood products. In some embodiments, the support 10 can be made waterproof.

In the illustrated embodiment of FIGS. 1-7, the support 10 comprises a body 12, a fastener 14, and a pivot element 52. The body 12 is comprised of a palmar portion 16, dorsal portion 18, external surface 28, and internal surface 30. The body 12 also has a longitudinal axis 68 generally parallel to the wearer's arm when inserted within the body 12, a transverse axis 70 perpendicular to the longitudinal axis 68 and generally parallel to the plane of the palm, and a vertical axis 72 generally perpendicular to the plane of the palm. The body 12 has a thickness 74 extending from the exterior surface 28 to the interior surface 30.

The palmar portion 16 and dorsal portion 18 are each further comprised of a distal end 20, proximal end 22, ulnar side 24, and radial side 26. The proximal end 22 is the end closer to the wearer's elbow and the distal end 20 is the end farther from the wearer's elbow. The ulnar side 24 is the side of the support 10 that is generally opposite from the medial plane of the human body when the arms are at rest with palms facing toward the posterior. In other words, the ulnar side 24 is on the side of the support 10 with the pinky finger on the hand. Conversely, the radial side 26 is the side of the support 10 that is generally closer to the medial plane of the human body when the arms are at rest with palms facing toward the posterior. That is, the radial side 26 is on the thumb side of the support 10.

In some embodiments, the body 12 can be of continuous construction; that is, the body 12 is a single unitary piece. In some embodiments, the body 12 is an assembly of a plurality of pieces. For example, in the illustrated embodiments the palmar portion 16 and the dorsal portion 18 are individual portions in a unitary construction that together form the body 12. In some embodiments, two, three, four, or more separate pieces are formed separately and attached together to form the body 12.

In the illustrated embodiment, the thickness 74 of the body 12 is generally uniform all around. Some embodiments include areas of increased or decreased thickness for various reasons, such as to save weight, add strength, or enhance comfort. For example, some embodiments use a palmar portion 16 that is thicker than the dorsal portion 18. Some embodiments have a dorsal portion 18 that is thicker than the palmar portion 16. Likewise, some embodiments have a distal end 20 that is thicker than the proximal end 22, and vice versa.

The illustrated embodiment has a solid, homogeneous thickness 74. In this embodiment there is no void or cavity between the exterior surface 28 and the interior surface 30. Alternate embodiments can have one or a plurality of cavities between these surfaces 28, 30, or the surfaces 28, 30 can be made of different materials or layers. The cavities can be empty or can be filled with various materials such as foam, rubber, cotton, down, gel, water, and combinations thereof. In some embodiments the cavities are filled with compressed air or other gases. Sometimes is it desirable to be able to change the rigidity of the support 10. Accordingly, some embodiments allow for adjustment of the amount of material and/or pressure inside the cavities. For example, some embodiments with air-filled cavities include a pump to add air and a valve to remove it.

The thickness 74 can vary according to the material used, whether the support wall is solid or has cavities, and the amount of rigidity sought. For instance, some embodiments with solid hard plastic have a uniform thickness of at least about 1/16". Some embodiments, including those utilizing gel-filled cavities, can have a thickness ranging from at least about 1/32 to at least about 1/4". Some embodiments, including those formed at least in part from metal can have a thickness of at least about 1/32" on the palmar 16 portion and at least about 1/16" on the dorsal portion.

The external and internal surfaces 28, 30 can generally closely follow the contours of a typical human hand to ensure a snug fit between the body 12 and the wearer's hand. In some embodiments, the exterior surface 28 is substantially smooth all around. Such a smooth surface can help avoid snags or scrapes caused by inadvertent contact between the support 10 and other objects or body parts. Other embodiments include a rough portion on at least a portion of the exterior surface 28 of the support 10. The rough portion may, for example, provide gripping assistance or facilitate a connection between the support 10 and other implements or components. In addition, for similar reasons, the interior surface 30 can be smooth or rough. In some instances, it is helpful to facilitate airflow or reduce weight, and some embodiments can include one or a plurality of penetrations or vents from the external surface 28 to the internal surface 30, and/or the interior surface 30 may include one or more raised portions, channels, or similar means to permit some level of ventilation between the hand, wrist, or arm, and the support 10.

A cushion 58 may be located on the interior surface 30. The cushion 58 can help secure the support 10 on the wrist by increasing the friction, contact surface area, or pressure between the support 10 and the wearer's skin and it can also help make the support 10 more comfortable to wear. In some embodiments, the cushion 58 covers a majority of or substantially the entire internal surface 30. Some embodiments utilize a plurality of cushions 58 arranged in spots, strips (as illustrated), or rings on the internal surface 30. The cushion 58 can be a resilient and soft material such as neoprene, rubber, cotton, wool, fabric, closed-cell foam, memory foam, natural or synthetic fur, leather, etc. Washable cushion materials can be advantageous. Some embodiments can include cushions 58 comprising bubble wrap or other types of sealed air padding. Some cushions 58 utilize thermal elastic, environmentally responsive, or other types of gel. Some embodiments include one or a plurality of O-rings.

Figure 1:
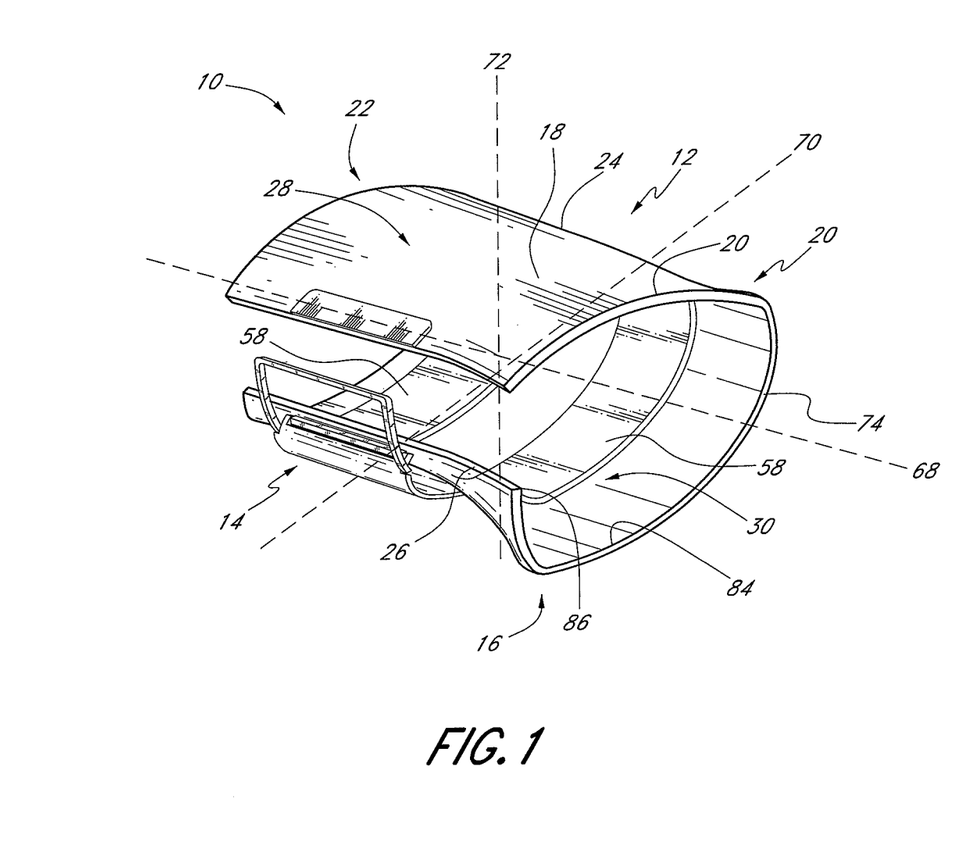
FIG. 1 is a perspective view of an embodiment of a wrist support.
Figure 1A:
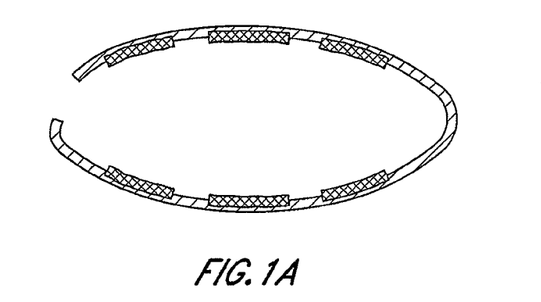
FIG. 1A is a cross-sectional view of an embodiment of FIG. 1.
Figure 2:
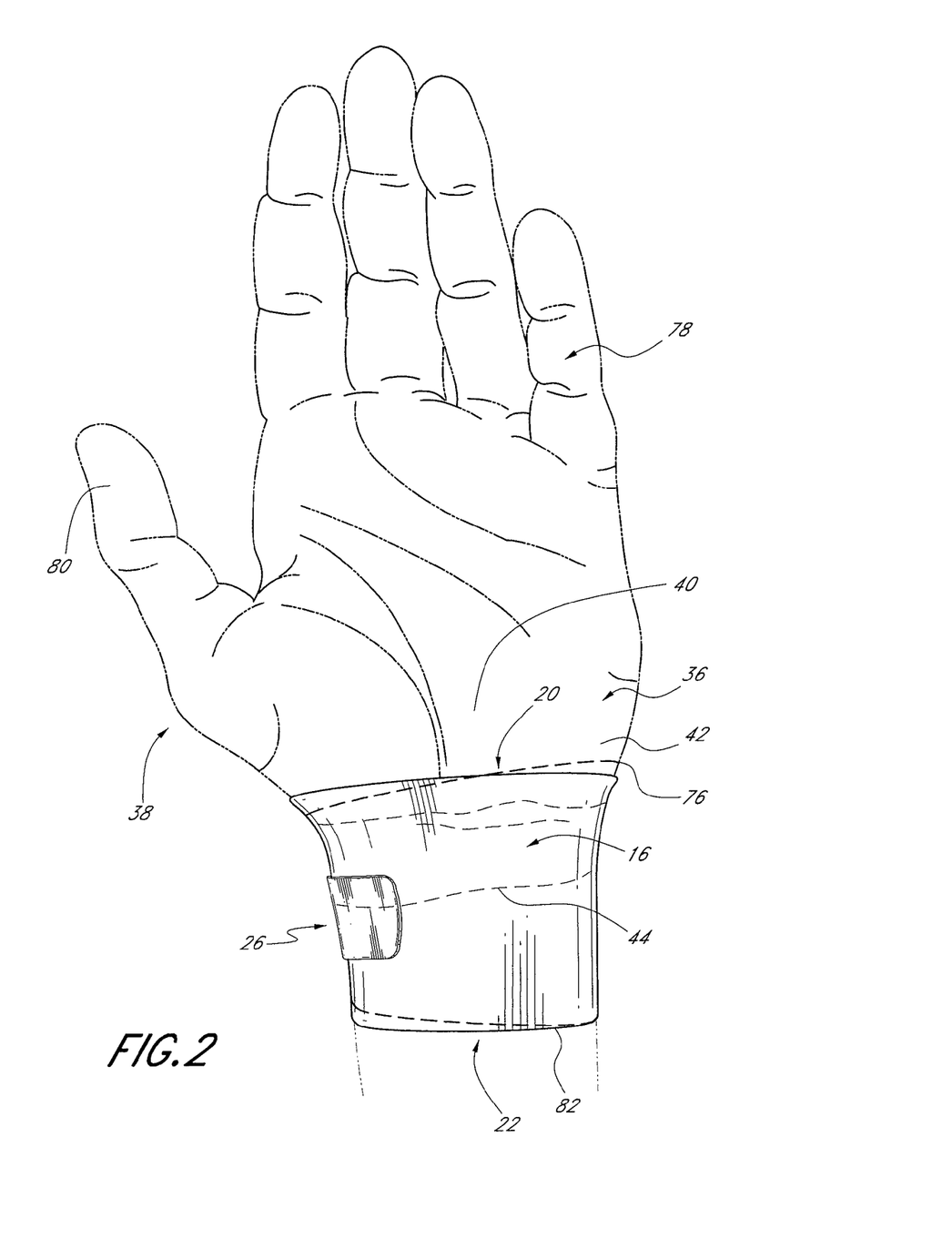
FIG. 2 is a side plan view of the palmar surface of the embodiment of FIG. 1.

In the plan view of FIG. 2, the palmar portion 16 of the illustrated embodiment has an overall substantially hourglass shape. The distal end 20 and the proximal end 22 can both be wider than a region positioned between these ends. The proximal end 22 can be narrower than the distal end 20. The proximal end 22 can be sized to fit an average size arm slightly below the wrist, while the distal end 20 can be sized to fit the base region of an average size hand slightly above the wrists. In the longitudinal direction 68 this shape is formed by the substantially convex or outwardly flared distal end 20 and proximal end 22. In the transverse direction 70, this shape is formed by the substantially concave ulnar side 24 and radial side 26. The distal end 20 of the palmar portion 16 may cover, in relation to the anatomy of the hand, portions of the hypothenar 36 and thenar 38. Some embodiments may cover, completely or in part, the palmar aponeurosis 40 ligament and/or palmar brevis 42 ligament. The proximal end 22 of the palmar portion 16 can extend in the longitudinal direction at least far enough to cover a portion of the wrist crease 44. All of the anatomical references herein can be determined using standard anatomical models for the target population for particular embodiment of the product.

In some embodiments, the support can terminate at the proximal end 22 slightly below the head of the radius bone (the so-called "wrist bump"). The distance from the wrist crease to the distal end 20 can be approximately the same as or slightly greater than the distance from the wrist crease to the proximal end 22. In the usage, the term "approximately the same as" is intended to encompass about +1½ inches. In the same embodiments, no additional structure is attached to or made integral with the support 10 on either the proximal or distal ends 20, 22. In other words, the support can terminate at the proximal and distal ends 20, 22. The support 10 can be made in different sizes to fit persons with different hand sizes.

Figure 3:
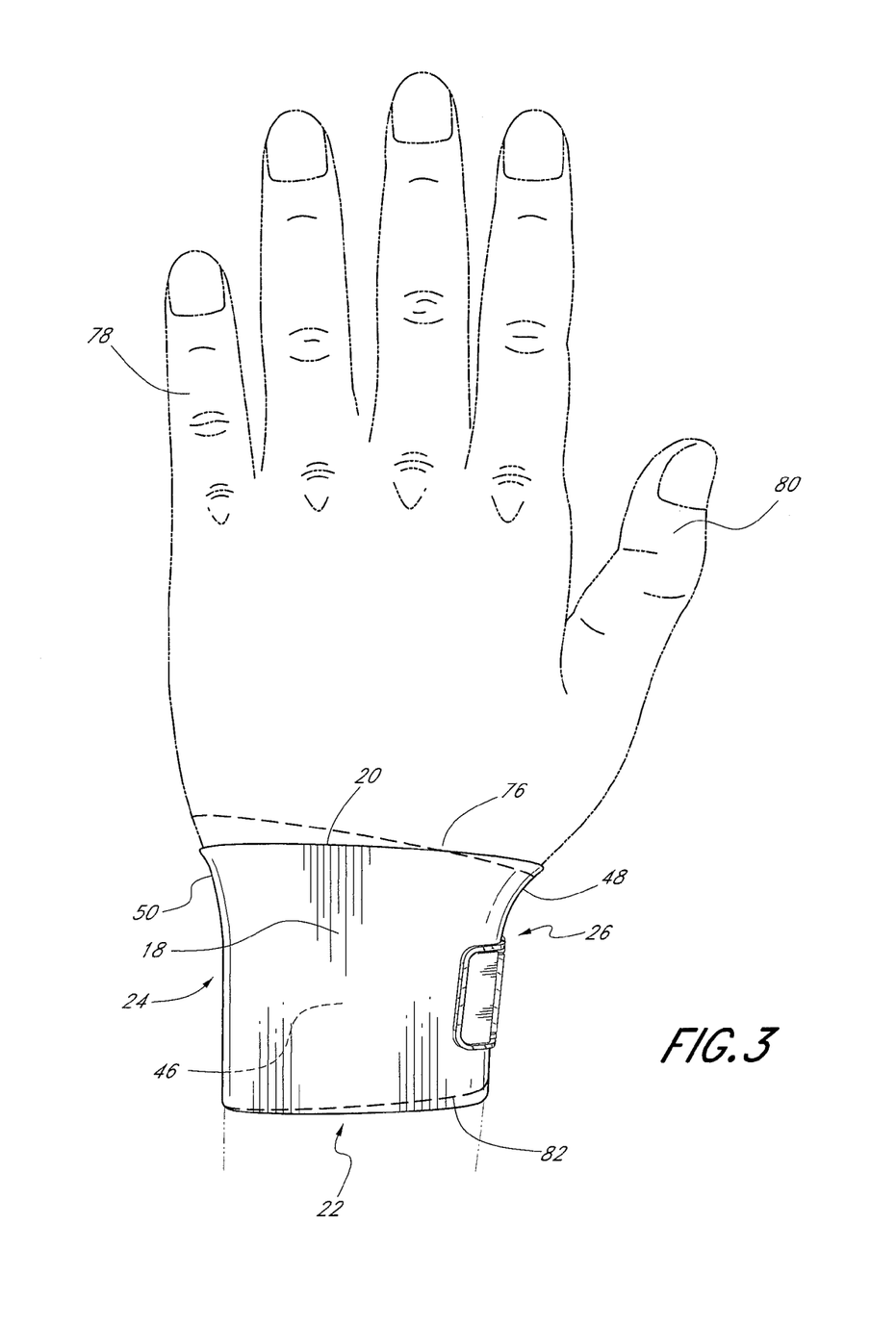
FIG. 3 is a side plan view of the dorsal surface of the embodiment of FIG. 1.
Figure 3A:
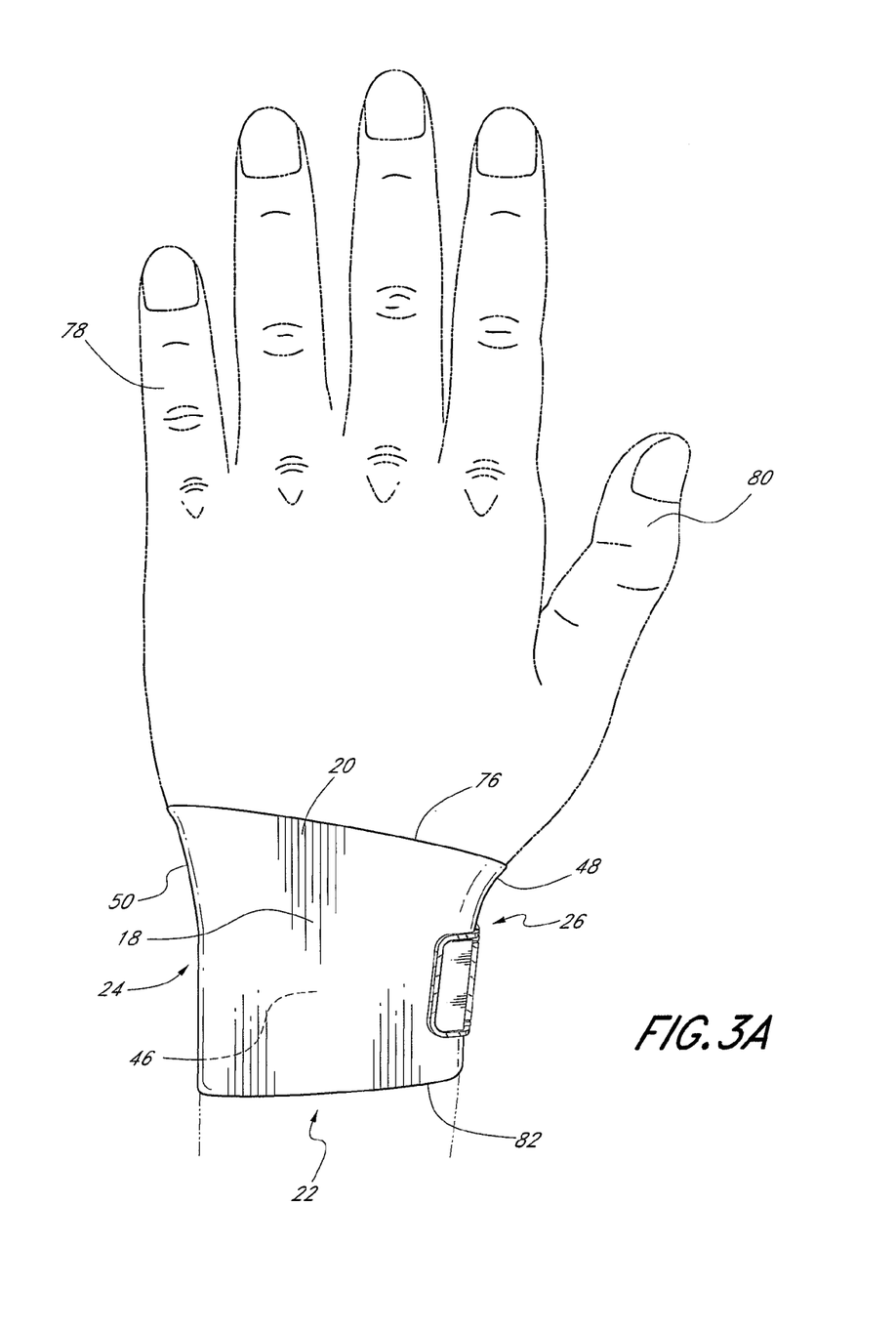

As shown in FIG. 3, the dorsal portion 18 of the illustrated embodiment also has an overall substantially hourglass shape in the plan view. In the longitudinal direction 68 this shape is formed by the substantially convex distal end 20 and proximal end 22. In the transverse direction 70, this shape is formed by the substantially concave ulnar side 24 and radial side 26. In relation to hand anatomy, the distal end 20 of the dorsal portion 18 of the illustrated embodiment can be made to cover, in whole or part, the dorsal carpal ligament 46. The proximal end 22 of the dorsal portion 18 can extend in the longitudinal direction at least far enough to cover all or a portion of the wrist crease 44 (see FIG. 2).

It can be helpful to allow the fingers and thumb to move unencumbered. Accordingly, the distal end 20 of the radial side 26 of either or both of the portions 16, 18 can curve outwardly about the base of the thumb. Thus, the thumb and fingers can be substantially free to move while the wrist is substantially restrained. The palmar portion 16 and the dorsal portion 18 can also have a distal end 20 which is contoured 76 such that the distal end 20 is higher on the ulnar side 24 than on the radial side 26. That is, the distal end 20 can be contoured closer to the pinky finger 78 and further away from the thumb 80. In some embodiments, this distal contour 76 can be equally close to the thumb 80 and pinky finger 78. Some embodiments include a concave distal contour 76 to further promote movement of the thumb and/or palm, and some embodiments have a substantially convex contour 76 to aid the palm also.

Similarly, the palmar portion 16 and the dorsal portion 18 can have a proximal end 22 which is contoured 82. FIGS. 2 and 3 show the proximal end contour 82 lower on the ulnar side 24 than on the radial side 26. That is, the proximal end 22 can be closer to the thumb 80 than to the pinky finger 78. In some embodiments, the proximal end contour is such that the proximal end 22 is equally close to the thumb 80 and pinky finger 78. In some embodiments the proximal contour 82 is convex and extends in the longitudinal direction toward the wearer's elbow to provide additional coverage and/or bracing on the wearer's arm. Some embodiments have a concave proximal contour 82 to allow flexion and/or extension of the wrist.

The length of the palmar portion 16 and dorsal portion 18, as measured along the longitudinal axis 68 at the transverse midpoint of the relevant portion, can vary according to the amount of support and restraint sought from the support and the size of the hand or arm designed to fit within it. For instance, some embodiments have a palmar portion 16 and dorsal portion 18 with a length of less than about 2". Other embodiments have a palmar portion 16 with a length of at least about 1¼" and a dorsal portion 18 with a length of at least about 2½". Yet other embodiments have a palmar portion 16 with a length of at least about 1¾" and a dorsal portion 18 with a length of at least about 1⅛". Some embodiments have a palmar portion 16 with a length of at least about 3" and a dorsal portion 18 with a length of at least about 2¼". In many embodiments, the length of the support on either or both of the palmar or dorsal sides 16, 18 is less than about 2¾'. It can be very useful in some embodiments for the support 10 to terminate or be free of any additional structures attached to the distal or proximal ends 10,22 so as to maximize the user's freedom of movements. Various other lengths can be used.

In the illustrated embodiment, in both the palmar and dorsal portions 16, 18, the transverse length of the distal end 20 is greater than the transverse length of the proximal end 22. In some embodiments, the length of these ends can be about equal. In some embodiments, the proximal end 22 that is wider than the distal end 20 in the transverse direction.

The distal end 20 and proximal end 22 can have edges 84 and corners 86. In the illustrated embodiment, these features 84, 86 are angular. However, to enhance comfort, the edges 84 and corners 86 can be smooth. For example, the edges 84 and corners 86 may be radiused or chamfered. Also, cushioning material may be fixed to the ends 20, 22 to cover the edges 84 and corners 86. Such cushioning materials may include, but are not limited to, plastic, soft rubber, and foam. Various other materials can be used, but washable materials and waterproof materials are preferred.

The radial side 26 can be contoured to generally follow the shape of a standard thumb side of the hand. Accordingly, the illustrated embodiment has an outward curve 48 as the radial side of the body 12 approaches the distal end 20. Similarly, the ulnar side 24 can be contoured to follow the shape of the pinkie side of the hand. Thus, the illustrated embodiment has an outward curve 50 as it approaches the distal end 20, with the radius of the curve 48 of the radial side 26 being less than the radius of the curve 50 of the ulnar side 24. In some embodiments, the curves 48, 50 can have about equal radii.

Figure 4:
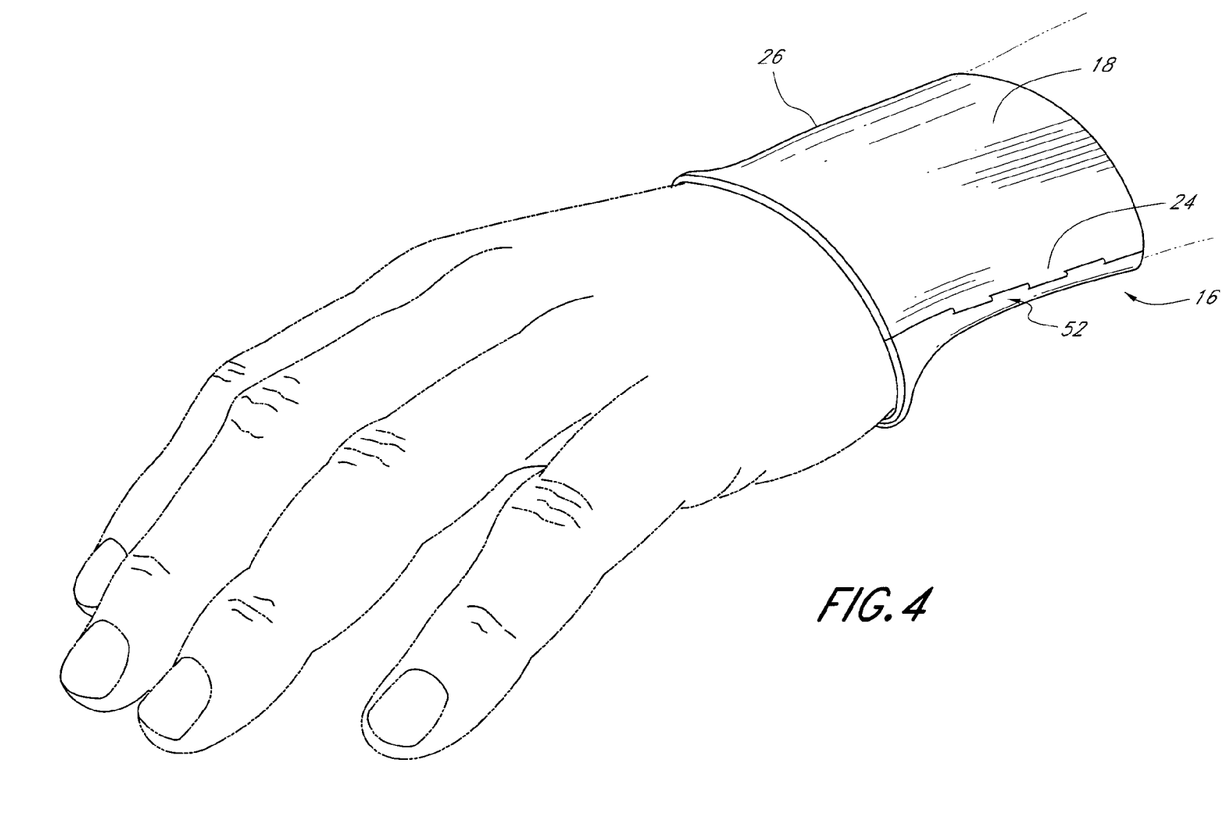
FIG. 4 is a perspective view of the ulnar side of an embodiment with a hinge.
Figure 5:
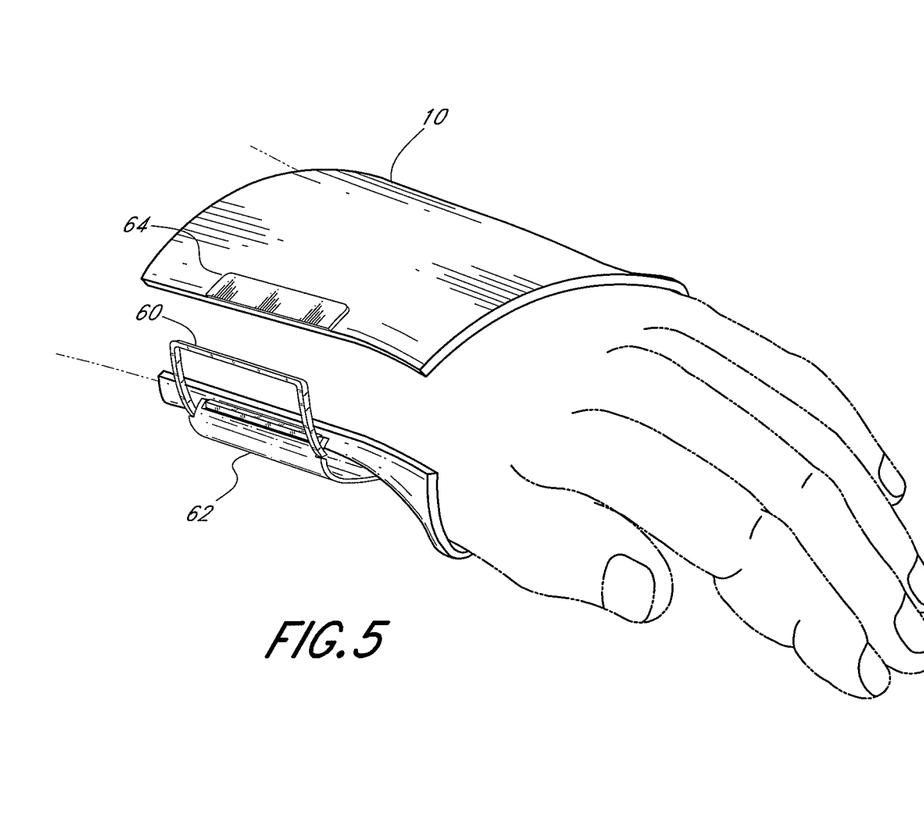
FIG. 5 is a perspective view of the embodiment of FIG. 1 being installed over a hand.

As shown in FIG. 4, the illustrated embodiment includes a pivot element 52 on the ulnar side 24 in the longitudinal direction 68. In some embodiments, the pivot element 52 can be located in any other location around the circumference of the body 12. For example, other embodiments can have the pivot element 52 located on the radial side 26. Some embodiments include the pivot element 52 in the palmar portion 16 and/or the dorsal portion 18. To facilitate removal of the support 10, sometimes it is helpful to have multiple pivot elements. For example, some embodiments have pivot elements 52 on both sides 24, 26. In some embodiments, such as those made from flexible materials, the support 10 can expand over a wearer's hand, and thus a distinct pivot element 52 may not be necessary. For instance, a body 12 made of spandex, or a resilient material such as a flexible plastic can be sized to snuggly fit the wearer's wrist and can also be expanded to fit over the wearer's hand. Such supports may not include a separate pivot element 52.

The pivot element 52 in the illustrated embodiment of FIG. 4 is a generally linear hinge that is substantially flush with the exterior portion 28 and interior portion 30 of the body 12. In the illustrated embodiment, the ulnar side 24 of the palmar portion 16 and dorsal portion 18 are sized and shaped to substantially interlock with one another to form the pivot element 52 and receive a hinge pin (not shown). Other embodiments can have different geometry and connection and/or movement means. For instance, in some embodiments, such interlocking of the portions 16, 18 does not occur and instead the sides of the portions 16, 18 abut in a substantially flush geometry with the pivot element 52 added as a separate component. In other embodiments, the portions 16, 18 do not directly join or abut, so the pivot element 52 bridges the gap and serves as the connection. In some embodiments, the portions 16, 18 overlap. The pivot element 52 can be substantially flush with the exterior surface 28 and interior surface 30 to avoid snagging.

Various types of pivots may be used, including but not limited to, pins, straps, butt hinges, slip hinges, pivot hinges, flush hinges, swaged hinges, and flanged hinges. In some embodiments the pivot 52 is spring-loaded to prevent or facilitate operation of the pivot 52 and thus opening/closing of the body 12. Some embodiments utilize one or a plurality of strips of flexible material as the pivot element 52. The pivot element 52 may be made of any suitable materials, including any water resistant and/or washable material such as plastic, nylon, polyester, neoprene, spandex, cotton, canvas, and metal.

As shown in FIGS. 5-7A, in some embodiments the body 12 is secured by a fastener 14. When the fastener 14 is in the open position, the body 12 can be expanded and thus be slipped over the user's hand and/or wrist. Conversely, movement of the support 10 is substantially prevented when the fastener 14 is closed. This is accomplished by the fastener 14 exerting compressive or tensile force on the body 12. Such forces can generally prevent the pivot element 52 from operating, so the body 12 cannot expand to fit over the wearer's hand and/or wrist. When the fastener 14 is released, the pivot element 52 is free to open so the body 12 can expand to facilitate installation or removal.

Figures 6, 6A:
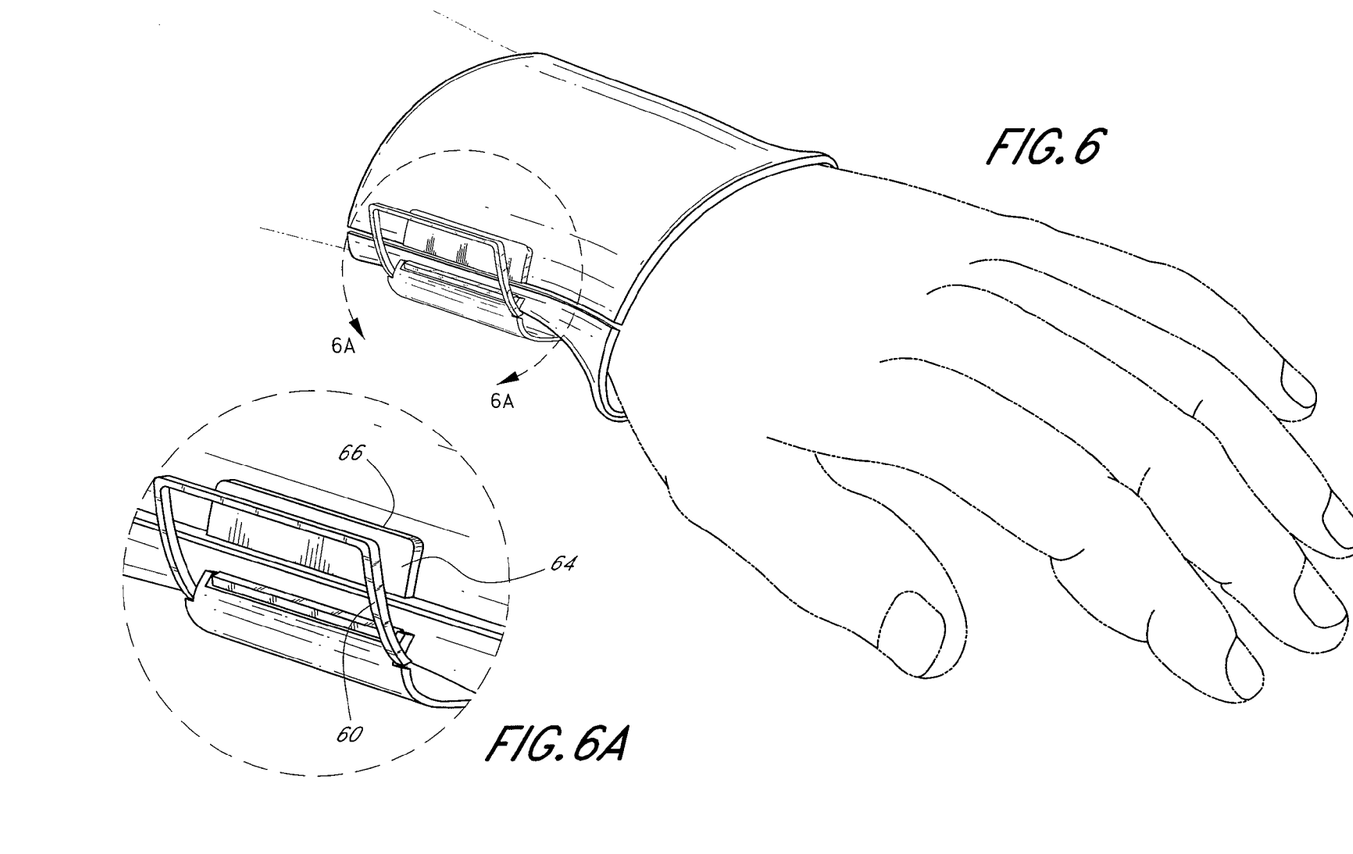
FIG. 6 is a perspective view of the embodiment of FIG. 1 installed on a hand in the closed, but not tightened, position.
FIG. 6A is a detail view of the clasping mechanism of the embodiment of FIG. 6 taken along the line 6A-6A.
Figures 7, 7A:
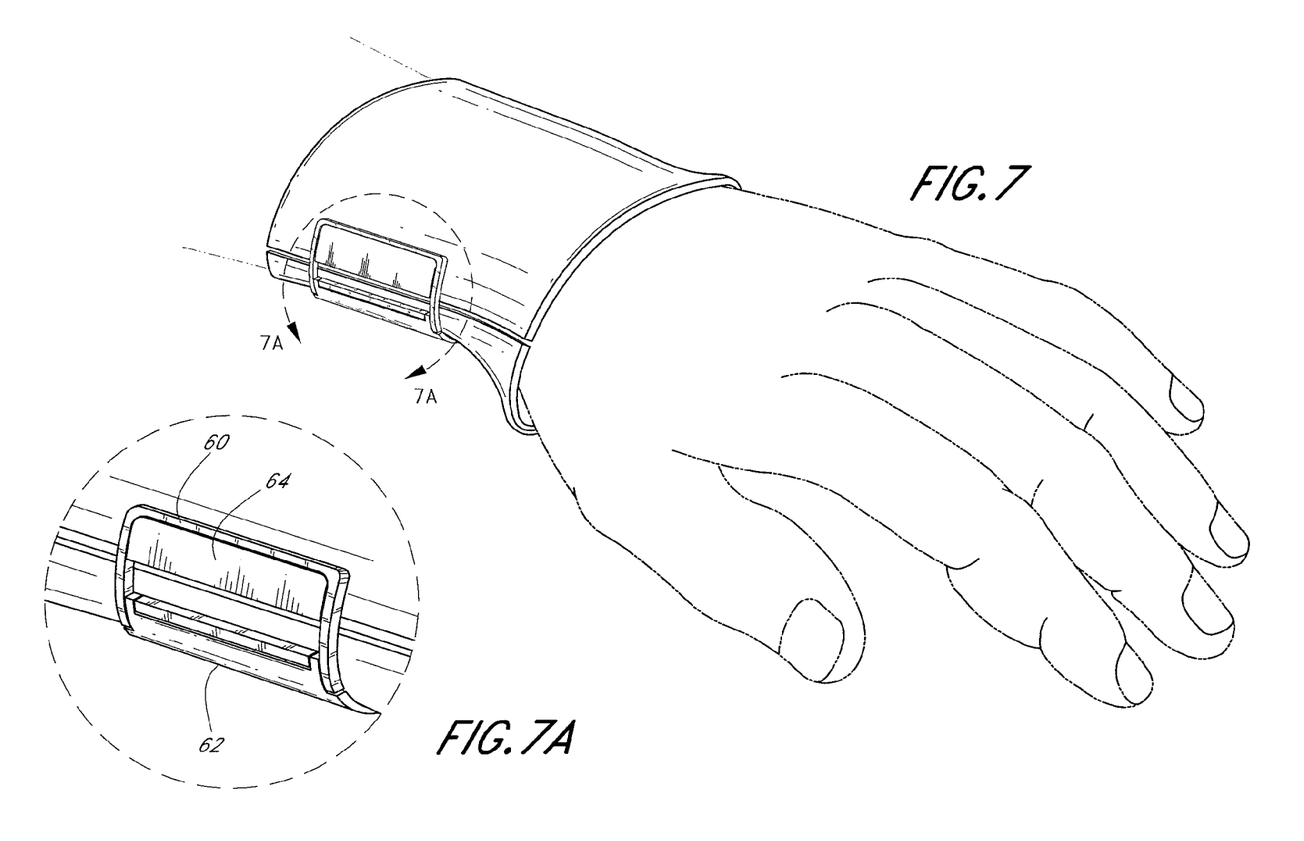
FIG. 7 is a perspective view of the embodiment of FIG. 1 installed on a hand in the closed and tightened position.
FIG. 7A is a detail view of the clasping mechanism of the embodiment of FIG. 7, taken along the line 7A-7A.

In the embodiment of FIGS. 6 and 7, the fastener 14 is a clasp comprising a clasping member 60, strap 62, and locking member 64. The clasping member 60 can be rotatably attached to an end of the strap 62. The opposite end of said strap can be fixed to the exterior surface 28 of the body 12. Both the clasp 60 and strap 62 can be located on either the palmar surface 16 or dorsal surface 18 while the locking member 64 can be located on the opposite surface therefrom. The locking member 64 can be positioned and sized and shaped to closely fit within the clasping member and contain a detent and/or lip 66 to lock the clasping member in place. Once the clasping member 60 is engaged with the locking member 64, the body 12 is held closed. The detent and/or lip 66, plus the force of the locking member 64 through the clasp 60 into the strap 62 onto the body 12, can inhibit or prevent the body 12 from opening. In some embodiments, the length of the strap 62 can be altered to allow for adjustment of the amount of force exerted by the fastener 14. Many other embodiments of a clasp can be used, with or without a fastener 14.

Such other clasp-type fasteners 14 can include deployment buckles, expansion bracelets, fold-over clasps, push-button clasps, jewelry clasps, and toggle clasps. Furthermore, many other types of fasteners can be used, including hook and loop fasteners, zippers, straps, buckles, buttons, hooks, snaps, laces, magnets, cotter pins, split pins, rivets, staples, elastic threads and/or cords, and combinations thereof. The fastener 14 can include one or many securing devices. For instance, some embodiments include one zipper and two snaps. Another embodiments have multiple straps and buckles. Some embodiments include hook and loop across all or substantially all of the longitudinal length of the body 12 and about 2" in the transverse direction.

In some embodiments, the fastener 14 is located on the radial side 26, while in other embodiments the fastener 14 is located on the ulnar side 24. A fastener 14 for a support 10 designed to be worn on the left hand can close towards the wearer's right hand. Conversely, a fastener 14 for a support 10 designed to be worn on the right hand can close towards the wearer's left hand. In some embodiments, the fastener 14 vertically protrudes from the body 12. In the closed position, the fastener 14 can be substantially flush with the exterior surface 28 of the body 12.

Some embodiments include features for attaching, retaining, and/or interfacing with accessories. For example, the support 10 may include one or a plurality of pockets. Some embodiments have, but are not limited to, snaps, hooks, laces, and/or magnets. Some embodiments have hook and loop fasteners. Accessories attached to, embedded in, or mounted on the support 10 may include, but are not limited to, tools, instruments, clocks, calculators, mirrors, vibration dampers, and heat shields. Accessories may also include radios, telephones or other communication devices, LCD or other viewing screens, navigation devices, notification or monitoring means, heart-rate monitors, GPS location determination devices, audio or video device (such as MP3 players), and/or e-mail receiving devices and other electronic devices.

Of course, it is to be understood that not necessarily all objectives or advantages described may be achieved in accordance with any particular embodiment described herein. Also, although the invention has been disclosed in the context of certain embodiments and examples, it will be understood by those skilled in the art that the invention extends beyond the specifically disclosed embodiments and/or uses and obvious modifications and equivalents thereof. Some embodiments can include one or more features described in connection with one or more of the embodiments described herein. Accordingly, the invention is not intended to be limited by the specific disclosures of preferred embodiments herein.

The following is claimed:

1. A wrist support comprising:
   a body member sized and shaped to closely fit around the wrist, comprising a palmar portion and a dorsal portion, wherein each portion has a distal end, a proximal end, a radial side, an ulnar side, and a thickness;
   the distal end terminating at a point adapted to be positioned below the thumb when worn, and the distal and being curved about the base of the thumb, adapted to extend toward the fingers more on the ulnar side than on the radial side,
   the proximal end terminating at a terminal proximal end adapted to be positioned slightly below the head of the radius bone when worn, the proximal end of the body member constituting the terminal proximal end of the wrist support, and wherein the distance from the distal end to the wrist crease is adapted to be approximately the same as or slightly greater than the distance from the wrist crease to the proximal end when worn;
   the body being formed of a rigid material that extends from the distal end to the proximal end and that is configured to surround the hand, a plurality of cavities positioned between an interior and exterior surface of the body, the cavities comprising gel;
   a pivot connecting the palmar and dorsal portions and allowing the palmar and dorsal portions to travel relative to each other; and
   a fastener.

2. The wrist support of claim 1, wherein the body member is constructed from one or more materials of the group comprising of metal, plastic, fabric, and combinations thereof.

3. The wrist support of claim 2, wherein the wrist support is substantially rigid.

4. The wrist support of claim 3, wherein the wrist support is substantially unbending in the longitudinal direction when positioned on a wearer.

5. The wrist support of claim 4, wherein the wrist support is configured to substantially prevent wrist movement when worn.

6. The wrist support of claim 5, wherein the wrist support is configured to completely immobilize the wrist when worn.

7. The wrist support of claim 5, wherein the wrist support is configured to help transfer forces applied to the hand to the larger and stronger muscles of the arm.

8. The wrist support of claim 4, wherein the wrist support is substantially unbending in the transverse direction when worn.

9. The wrist support of claim 1, wherein the body member is constructed from hard plastic.

10. The wrist support of claim 1, wherein the body member is made of a continuous construction.

11. The wrist support of claim 1, wherein the body member is comprised of a plurality of pieces.

12. The wrist support of claim 1, wherein an inner surface comprises a cushion.

13. The wrist support of claim 1, wherein the pivot is a hinge.

* * * * *

UNITED STATES PATENT AND TRADEMARK OFFICE
CERTIFICATE OF CORRECTION

PATENT NO.        : 8,641,650 B2
APPLICATION NO.   : 12/411194
DATED             : February 4, 2014
INVENTOR(S)       : Spitzer Page 1 of 1

It is certified that error appears in the above-identified patent and that said Letters Patent is hereby corrected as shown below:

In the Specification

Column 4 line 38, Change "+11/2" to --+1-1/2--.

In the Claims

Column 8 line 3, In Claim 1, after "fit" insert --circumferentially--.

Column 8 line 7, In Claim 1, after "end" insert --of the body member--.

Column 8 line 8, In Claim 1, after "below" insert --a base region of--.

Column 8 line 8, In Claim 1, change "and" to --end--.

Column 8 line 9, In Claim 1, after "toward" delete "the".

Column 8 line 10, In Claim 1, change "side," to --side;--.

Signed and Sealed this
Twenty-sixth Day of August, 2014

Michelle K. Lee
*Deputy Director of the United States Patent and Trademark Office*